US010899996B2

(12) United States Patent
Liniger

(10) Patent No.: US 10,899,996 B2
(45) Date of Patent: Jan. 26, 2021

(54) ORGANIC COMPOUNDS

(71) Applicant: GIVAUDAN SA, Vernier (CH)

(72) Inventor: Marc Liniger, Embrach (CH)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 16/629,248

(22) PCT Filed: Jul. 25, 2018

(86) PCT No.: PCT/EP2018/070165

§ 371 (c)(1),
(2) Date: Jan. 7, 2020

(87) PCT Pub. No.: WO2019/020691

PCT Pub. Date: Jan. 31, 2019

(65) Prior Publication Data

US 2020/0140779 A1 May 7, 2020

(30) Foreign Application Priority Data

Jul. 26, 2017 (GB) .................................. 1712014.8

(51) Int. Cl.
*A61K 8/00* (2006.01)
*A61K 8/18* (2006.01)
*A61Q 13/00* (2006.01)
*C11B 9/00* (2006.01)

(52) U.S. Cl.
CPC .................................. *C11B 9/008* (2013.01)

(58) Field of Classification Search
CPC ..................................................... C11B 9/008
USPC ................................................... 512/11, 8, 1
See application file for complete search history.

(56) References Cited

U.S. PATENT DOCUMENTS

2011/0295024 A1 12/2011 Gralla
2016/0096814 A1* 4/2016 Schrems ............. C07D 309/18 549/356

FOREIGN PATENT DOCUMENTS

| | | | |
|---|---|---|---|
| EP | 0082401 A1 | 6/1983 | |
| GB | 2036004 B | 6/1980 | |
| WO | 7900509 A1 | 8/1979 | |
| WO | 2009077550 A1 | 6/2009 | |
| WO | 2014184311 A1 | 11/2014 | |
| WO | WO-2014184311 A1 * | 11/2014 | .......... B01J 31/0225 |

OTHER PUBLICATIONS

G. Ohloff, et al, Synthesis of R and (S) 4 Methyl 6-2-Methylprop-1-Enyl-5-6-Dihydro-2H-Pyran . . . , Helvetica Chimica, vol. 63, No. 6, Jan. 1, 1980, pp. 1586-1587.

L. Luping, et al, " a General Catalytic Asymmetric Prins Cyclization", Journal of American Chemical Society, vol. 138, No. 34, Aug. 31, 2018.

International Search Report and Written Opinion of the International Searching Authority for Corresponding Application PCT/EP2018/070165 dated Oct. 15, 2018.

GB Search Report for Corresponding Application GB1712014.8 dated Jan. 29, 2018.

* cited by examiner

*Primary Examiner* — Jessica Whiteley
(74) *Attorney, Agent, or Firm* — Norris McLaughlin PA

(57) ABSTRACT

The use as fragrance ingredient of 4—methylene—2—(2—methylprop—1—enyl)—tetrahydropyran.

6 Claims, No Drawings

ORGANIC COMPOUNDS

This disclosure relates to fragrance compositions and to a method of their preparation.

Rose oxide (2-(2-methylprop-1-enyl)-4-methyltetrahydropyran) is a well-known and desirable fragrance material, used in cosmetic products and detergents. There are a number of different methods of producing this material, one of them being the selective hydrogenation of dehydro rose oxide (4-methylene-2-(2-methylprop-1-enyl)-tetrahydropyran). This is described, for example, in International Publication WO 79/00509. Dehydro rose oxide is considered to be an important intermediate for the production of rose oxide, and methods for making it have been described (for example, International Publication WO 2014/184311). Whereas dehydro rose oxide is a valuable intermediate for the production of rose oxide, the undesirable nerol oxide as a by-product is always formed.

Even though it is mentioned in the literature that dehydro rose oxide can be isolated and purified, this to the best of our knowledge, has never been done, for the simple reason that each additional process step would have increased the production costs of rose oxide. Thus, only crude reaction products comprising solvents, by-products and possibly unreacted starting material, are disclosed in the literature. Dehydro rose oxide has never been considered as a fragrance material, and its use as a fragrance material is, to the best of our knowledge, nowhere described.

It has now been surprisingly found that dehydro rose oxide can be useful as a fragrance material in its own right, and not merely as an intermediate, providing a fragrance material of outstanding and desirable olfactory characteristics.

Surprisingly it was found that dehydro rose oxide possesses a very powerful green, rosy, rose oxide like, metallic odor profile. Dehydro Rose Oxide has an GC-odor threshold value that is almost 300 times lower compared to Nerol Oxide and about 5 times lower compared to Rose Oxide.

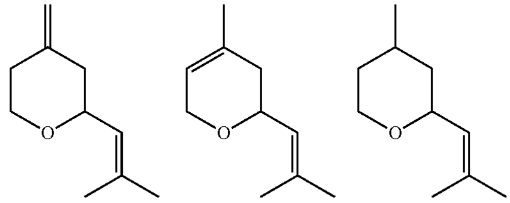

Dehydro Rose Oxide Nerol Oxide Rose Oxide

As used herein, "odor threshold value" means the lowest concentration of a vapour in the air which can be detected by smell. Generally speaking, it can be said that a compound with a low odor threshold value is more powerful than a compound with a high odor threshold value and thus allows the use of very low concentration in a fragrance composition to achieve an olfactory effect.

Thus there is provide in a first aspect the use of 4-methylene-2-(2-methylprop-1-enyl)-tetrahydropyran (dehydro rose oxide) as a fragrance ingredient.

A number of methods for the preparation of dehydro rose oxide have been described, one recent example being that of the abovementioned WO 2014/184311. The method disclosed therein only describes a mixture of dehydro rose oxide with nerol oxide in toluene.

Whereas nerol oxide (3,6-dihydro-4-methyl-2-(2-methylprop-1-en-1-yl)-2H-pyran) is a known fragrance ingredient having an odour described as "green, weedy, cortex, herbal, narcissus, celery", toluene possess a sweet, pungent, benzene-like odor, which may explain why the potential of dehydro rose oxide as fragrance ingredient was never recognized. It is well known that, for process optimizations, only small samples are taken of the reaction mixture to analyze the conversion, yield and selectivity, prior to the transfer of the crude mixture to the next process step.

To be suitable as fragrance ingredient, it is important that dehydro rose oxide is essentially free of impurities which negatively affect the odor profile, such as 3-methylbut-2-enal or 3-methylbut-3-en-1-ol. Whereas it is possible to obtain the pure dehydro rose oxide from the crude mixture by repeated fractional distillation, preferably with high columns containing structured packing (e.g. Sulzer column)—which is laborious and expensive, and for most practical purposes not worthwhile—a purification by standard distillation, such as a Vigreux column is sufficient to obtain a mixture consisting essentially of dehydro rose oxide and nerol oxide, which is essentially free of off-notes.

Thus there is provided in a further aspect a fragrance mixture consisting essentially of dehydro rose oxide and nerol oxide, e.g., at a weight ratio from 99:1 to 1:99 (which includes 95:5 to 5:95, 9:1 to 1:9 mixtures, 8:2 to 2:8 mixtures, 7:3 to 3:7 mixtures, 3:2 to 2:3 mixtures, and 1:1 mixtures). A mixture enriched in dehydro rose oxide is preferred, such as mixtures at a weight ratio from 2:1 to 5:1 (which includes mixtures at a weight ratio of 4:1).

Already mixtures of dehydro rose oxide and nerol oxide at a weight ratio of about 4:1 are superior with regard to its olfactometric odor detection threshold compared to rose oxide.

There is additionally provided a method of improving, enhancing or modifying a consumer product base by means of addition thereto of an olfactory acceptable amount of dehydro rose oxide, or a fragrance composition comprising dehydro rose oxide.

In a further aspect there is provided a fragrance application comprising dehydro rose oxide as a fragrance-providing material, and a consumer product base.

By "fragrance composition" is meant any composition comprising dehydro rose oxide and a base material.

As used herein, the "base material" includes all known fragrance ingredients selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, diluents, and other auxiliary agents commonly used in the art.

As used herein, "carrier material" means a material which is practically neutral from a odorant point of view, i.e. a material that does not significantly alter the organoleptic properties of odorants.

By "diluents" is meant any diluent conventionally used in conjunction with odorants, such as diethyl phthalate (DEP), dipropylene glycol (DPG), isopropyl myristate (IPM), triethyl citrate (TEC) and alcohol (e.g. ethanol).

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same, such as anti-oxidant adjuvant. Said anti-oxidant may be selected, for example, from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

It might also be an ingredient that provides additional benefits such as imparting color or texture. It might also be an ingredient that imparts light resistance or chemical stability to one or more ingredients contained in a fragrance composition.

A detailed description of the nature and type of auxiliary agent commonly used in fragrance compositions containing same cannot be exhaustive, but it has to be mentioned that said ingredients are well known to a person skilled in the art.

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, eucalyptus oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants.

Cosmetic products include:

(a) cosmetic skincare products, especially bath products, skin washing and cleansing products, skincare products, eye makeup, lip care products, nail care products, intimate care products, foot care products;

(b) cosmetic products with specific effects, especially sunscreens, tanning products, de-pigmenting products, deodorants, antiperspirants, hair removers, and shaving products;

(c) cosmetic dental-care products, especially dental and oral care products, tooth care products, cleaners for dental prostheses, adhesives for dental prostheses; and (d) cosmetic hair care products, especially hair shampoos, hair care products, hair setting products, hair-shaping products, and hair coloring products.

This list of products is given by way of illustration, and is not to be regarded as being in any way limiting.

Dehydro rose oxide may be used alone or blended with one or more of the many fragrance ingredients known to the art and readily available commercially from the major fragrance manufacturers. Non-limiting examples of such ingredients include

- essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;
- alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;
- aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl)but-3-en-2-one); 3-(4-isobutyl-2-methylphenyl)propanal; maltol; methyl cedryl ketone; methylionone; verbenone; and/or vanillin;
- ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1,3]dioxane]);
- macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and
- heterocycles, e.g. isobutylquinoline (2-isobutylquinoline).

Dehydro rose oxide may be used in a broad range of fragrance applications, for example, in any field of fine and functional perfumery, such as perfumes, household products, laundry products, body care products and cosmetics. Specific exemplary and non-limiting examples include as fine fragrances, e.g. eaux de perfume and eaux de toilette; household products, e.g. detergents for dishwasher, surface cleaner, air freshener; laundry products, e.g. softener, bleach, detergent; body care products, e.g. after-shave lotion, shampoo, shower gel, shower and bath salt, hygiene product; and cosmetics, e.g. deodorants, vanishing creams, comprising an odorant.

Dehydro rose oxide may be used in a broad range of fragrance applications, e.g. in any field of fine and functional perfumery, such as perfumes, air care products, household products, laundry products, body care products and cosmetics. The compound can be employed in widely varying amounts, depending upon the specific article and on the nature and quantity of other odorant ingredients. The proportion is typically from 0.0001 to 30 weight percent of the article. In one embodiment, the dehydro rose oxide may be employed in a fabric softener in an amount from 0.001 to 0.3 weight percent (e.g. 0.01 to 0.1 including 0.05 weight %). In another embodiment, dehydro rose oxide may be used in fine perfumery in amounts from 0.01 to 30 weight percent (e.g. up to about 10 or up to 20 weight percent), more preferably between 0.01 and 5 weight percent. However, these values are given only by way of example, since the experienced perfumer may also achieve effects or may create novel accords with lower or higher concentrations.

In the formulation of fragrance applications, there may also be used any of the known ingredients used in such applications, non-limiting examples including surfactants, solvents, pigments, dyestuffs, extenders, thickeners, rheology modifiers and the like.

Fragrance compositions comprising dehydro rose oxide may, as mentioned hereinabove, be employed into the fragrance application simply by directly mixing the fragrance composition with a fragrance application base. Alternatively, the fragrance compositions may be used in entrapped form, in one or more of the available entrapment materials such as polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzymes, or the like, and then mixed with the application. The combination of the fragrance application ingredients, including the fragrance compositions hereinabove defined, may be in any desired order using any known method.

The disclosure is now further described with reference to the following non-limiting examples.

Example 1: Dehydro Rose Oxide

A round-bottomed flask equipped with a Dean-Stark trap was charged with toluene (60 mL) and an aqueous solution of $NaHSO_4$ (0.56 mL, 10% in water, 56 mg, 0.2 mol %). The reaction mixture was preheated to reflux (150° C. oilbath), while a 1:1 mixture of neat 3-methylbut-3-en-1-ol (23.5 ml, 232 mmol, 1.0 equiv) and 3-methylbut-2-enal (19.5 g, 232 mmol, 1.0 equiv) was added with a syringe pump (10 mL/h). After refluxing over night, an additional amount of a 10% $NaHSO_4$ solution (0.5 mL, 56 mg, 0.2 mol %) was added at room temperature to the reaction mixture and refluxing was continued for 4 h. A total amount of 3.5 mL of water was collected in the trap. The reaction mixture was allowed to cool to room temperature and extracted with MTBE, washed with diluted aq. 0.02M NaOH, water and brine, dried over $MgSO_4$ and filtered. The solvent was removed under reduced pressure. The crude product (33 g) was purified by Kugelrohr distillation (120° C. at 8 mbar) to give a mixture of dehydro rose oxide (DHRO) and nerol oxide (NO) (19.5 g, 55% chemical yield, DHRO/NO 63:25, 88% purity by GC). For the olfactive quality, the product was repurified by fractional distillation over a 10 cm Vigreux column to afford a mixture of dehydro rose oxide (DHRO) and nerol oxide (NO) (10.8 g, 31% olfactive yield, 85:15 DHRO/NO, bp: 55-57° C. at 8 mbar) as a colorless liquid. In addition, a second fraction containing a higher content of nerol oxide NO (3.2 g, 9% yield, DHRO/NO 60:40, bp: 60° C. at 8 mbar) was isolated.

Analytical data for dehydro rose oxide (DHRO):

$^1$H-NMR (400 MHz, $CDCl_3$, δ/ppm): 5.23-5.15 (m, 1H), 4.74-4.67 (m, 2H), 4.04 (ddd, J=1.7, 5.6, 11.0 Hz, 1H), 3.94 (ddd, J=2.7, 8.1, 10.8 Hz, 1H), 3.40 (ddd, J=2.7, 11.0, 12.1 Hz, 1H), 2.35-2.23 (m, 1H), 2.20-2.01 (m, 3H), 1.71 (d, J=1.5 Hz, 3H), 1.66 (d, J=1.5 Hz, 3H). $^{13}$C-NMR (101 MHz, $CDCl_3$, δ/ppm): 144.5, 136.0, 125.6, 108.3, 75.7, 68.3, 41.2, 34.9, 25.7, 18.3. GC-MS (ESI, m/z): 152 ($M^+$, 42), 137 (100), 107 (15), 85 (60), 83 (18), 67 (58), 53 (23), 41 (31), 40 (19), 39 (35), 29 (14), 27 (14).

Odor description: green, rosy, rose oxide like, metallic

Analytical data for nerol oxide (NO):

$^1$H-NMR (400 MHz, $CDCl_3$, δ/ppm): 5.42-5.35 (m, 1H), 5.25-5.16 (m, 1H), 4.24-4.11 (m, 3H), 2.09-1.95 (m, 1H), 1.85-1.76 (m, 1H), 1.73 (d, J=1.5 Hz, 3H), 1.70-1.66 (m, 6H). $^{13}$C-NMR (101 MHz, $CDCl_3$, δ/ppm): 135.9, 131.8, 125.7, 119.6, 70.6, 65.5, 35.9, 25.7, 22.9, 18.3. GC-MS (ESI, m/z (%)): 152 ($M^+$, 7), 109 (7), 96 (11), 85 (31), 83 (82), 69 (20), 68 (100), 67 (91), 53 (26), 41 (36), 39 (36), 29 (22), 27 (18).

Odor description: green, weedy, cortex, herbal, narcissus, celery

Example 2: Fragrance Formulation

| | Parts by weight |
|---|---|
| Ethyl Cyclohexyl Acetate | 5 |
| Acetophenone | 0.5 |
| Agrumex ™ (2-(tert-butyl)cyclohexyl acetate) | 26 |
| Phenyl Ethyl Alcohol (2-phenylethan-1-ol) | 110 |
| Hydratropicaldehyde Dimethylacetal (1,1-dimethoxypropan-2-yl)benzene) | 16 |
| L-Carvone | 4 |
| Citronellol | 122 |
| Cyclal ™ C (2,4-dimethylcyclohex-3-ene-1-carbaldehyde) | 5 |
| Dihydro Myrcenol | 105 |
| Diphenyl Oxide | 9 |
| Dipropylene Glycol | 11 |
| Estragole ™ (1-allyl-4-methoxybenzene) | 10 |
| Gardenol ™ (1-phenylethyl acetate) | 12 |
| Hedione ™ (methyl 2-(3-oxo-2-pentylcyclopentyl)acetate) | 3 |
| Isopentyrate (4-methylpent-4-en-2-yl isobutyrate) | 5 |
| Jasmacyclene ™ (3a,4,5,6,7,7a-hexahydro-1H-4,7-methanoinden-6-yl acetate) | 60 |
| Lilial ™ (3-(4-(tert-butyl)phenyl)-2-methylpropanal) | 80 |
| Linalool | 230 |
| Manzanate ™ (ethyl 2-methylpentanoate) | 4 |
| Menthone (2-isopropyl-5-methylcyclohexan-1-one) | 12 |
| Peach Pure (5-heptyldihydrofuran-2(3H)-one) | 0.5 |
| Rose Oxide | 14 |
| Hexyl Salicylate | 40 |
| Serenolide ™ (2-(1-(3,3-dimethylcyclohexyl)ethoxy)-2-methylpropyl cyclopropanecarboxylate | 6 |
| Terpineol Pure (2-(4-methylcyclohex-3-en-1-yl)propan-2-ol) | 60 |
| Total: | 950 |

The formula was also prepared with the 14 parts of rose oxide being substituted by 14 parts of a 85:15 weight ratio mixture of dehydro rose oxide and nerol oxide, prepared according to Example 1.

The replacement of Rose Oxide resulted in a fragrance formulation described as being more green petitgrain, vegetable-like, and more powerful than the formulation comprising Rose oxide.

The invention claimed is:

1. A fragrance material comprising 4-methylene-2-(2-methylprop-1-enyl)-tetrahydropyran in combination with nerol oxide at a weight ratio of from 99:1 to 8:2.

2. A fragrance mixture consisting essentially of 4-methylene-2-(2-methylprop-1-enyl)-tetrahydropyran and nerol oxide at a weight ratio of from 99.1 to 8:2.

3. A fragrance application comprising the fragrance material of claim 1, and a consumer product base.

4. The fragrance application of claim 3 wherein the consumer product base is selected from the group consisting of fine perfumery, fabric care, household products and personal care products.

5. A method of improving, enhancing or modifying a consumer product base comprising:

adding to the consumer product base an olfactory acceptable amount of 4-methylene-2-(2-methylprop-1-enyl)-tetrahydropyran.

6. The method of claim 5 in which there is additionally present nerol oxide, and the 4-methylene-2-(2-methylprop-1-enyl)-tetrahydropyran and nerol oxide are present in a respective weight ratio of from 99:1 to 8:2.

* * * * *